US012245919B2

(12) United States Patent
Carty et al.

(10) Patent No.: US 12,245,919 B2
(45) Date of Patent: Mar. 11, 2025

(54) MEDICAL ADHESIVES FOR QUICK RELEASE OF ANTIMICROBIALS

(71) Applicant: Avery Dennison Corporation, Glendale, CA (US)

(72) Inventors: Neal Carty, Chicago, IL (US); Jilin Zhang, Mentor, OH (US)

(73) Assignee: Avery Dennison Corporation, Mentor, OH (US)

( * ) Notice: Subject to any disclaimer, the term of this patent is extended or adjusted under 35 U.S.C. 154(b) by 836 days.

(21) Appl. No.: 17/251,160

(22) PCT Filed: Jun. 12, 2019

(86) PCT No.: PCT/US2019/036771
§ 371 (c)(1),
(2) Date: Dec. 10, 2020

(87) PCT Pub. No.: WO2019/241391
PCT Pub. Date: Dec. 19, 2019

(65) Prior Publication Data

US 2021/0259890 A1 Aug. 26, 2021

Related U.S. Application Data

(60) Provisional application No. 62/684,459, filed on Jun. 13, 2018.

(51) Int. Cl.

| | |
|---|---|
| ***A61F 13/0246*** | (2024.01) |
| ***A61F 13/00*** | (2024.01) |
| ***A61L 15/18*** | (2006.01) |
| ***A61L 15/28*** | (2006.01) |
| ***A61L 15/46*** | (2006.01) |
| ***A61L 15/58*** | (2006.01) |
| ***C08L 1/02*** | (2006.01) |

(52) U.S. Cl.
CPC .......... *A61F 13/0253* (2013.01); *A61L 15/18* (2013.01); *A61L 15/28* (2013.01); *A61L 15/46* (2013.01); *A61L 15/58* (2013.01); *C08L 1/02* (2013.01); *A61F 2013/00663* (2013.01); *A61F 2013/00702* (2013.01); *A61F 2013/0091* (2013.01); *A61L 2300/206* (2013.01); *A61L 2300/232* (2013.01)

(58) Field of Classification Search
None
See application file for complete search history.

(56) References Cited

U.S. PATENT DOCUMENTS

| | | | |
|---|---|---|---|
| 8,877,882 | B1 | 11/2014 | Salamone et al. |
| 9,346,981 | B2 | 5/2016 | Wibaux et al. |
| 10,456,498 | B2 | 10/2019 | Wibaux |
| 11,147,722 | B2 | 10/2021 | Zhou et al. |
| 2007/0020319 | A1 | 1/2007 | Bougherara |
| 2010/0121304 | A1 | 5/2010 | Zhou et al. |
| 2013/0303656 | A1 | 11/2013 | Wibaux et al. |
| 2014/0031734 | A1 | 1/2014 | Saxena et al. |
| 2015/0367021 | A1 | 12/2015 | Wibaux |
| 2016/0038629 | A1 | 2/2016 | Carty |
| 2017/0087270 | A1 | 3/2017 | Wibaux |
| 2021/0059890 | A1 | 3/2021 | Boyd |

FOREIGN PATENT DOCUMENTS

| | | |
|---|---|---|
| CA | 1337970 | 1/1996 |
| CN | 1647786 | 8/2005 |
| CN | 101805940 | 8/2010 |
| CN | 102209509 | 10/2011 |
| CN | 102665403 | 9/2012 |
| CN | 103442572 | 12/2013 |
| CN | 106178087 | 12/2016 |
| EP | 0361722 | 12/1993 |
| JP | 2002-272831 | 9/2002 |
| JP | 2016-511310 | 4/2016 |
| JP | 2016-539670 | 12/2016 |
| WO | 2011/009083 | 7/2010 |
| WO | 2012/100244 | 7/2012 |

OTHER PUBLICATIONS

International Preliminary Report on Patentability dated Dec. 15, 2020 issued in corresponding IA No. PCT/US2019/036771 filed Jun. 12, 2019.
International Search Report and Written Opinion dated Oct. 7, 2019 issued in corresponding IA No. PCT/US2019/036771 filed Jun. 12, 2019.
Chinese Medical Encyclopedia, Tongjin Tu, 1995, p. 1305.
Fine Organic Chemistry, Anshun Peng et al., 1996, p. 172.
Textile Applied Chemistry and Experiments, Tianrong Wu, 2003, pp. 127-128.
2003 Health Professional Technical Qualification Examination Guidelines for Preventive Medicine Major Technicians, compiled by the National Health Professional Technical Qualification Examination Expert Committee, 2003, pp. 335-336.
Field Guide to Urgent and Ambulatory Care Procedures, edited by David M. James (U.S.), translated by Zhanhong Wang et al., 2004, pp. 268.
Pharmaceutics (3rd Edition), Xide Tu et al., 1985, pp. 693-698.

*Primary Examiner* — Kyung S Chang

(57) ABSTRACT

Provided herein are adhesive compositions comprising: 1) at least one adhesive of an alcohol-functionalized acrylic adhesive, an alcohol-functionalized silicone adhesive, a carboxyl-functionalized acrylic adhesive, and a carboxyl-functionalized silicone adhesive, 2) at least one phase-separated hydrophilic material, and 3) at least one bioactive compound. At least one bioactive compound may comprise an antimicrobial agent. The adhesive compositions can quickly release an antimicrobial agent and cause the rapid onset of antimicrobial effects. Also provided are adhesive products and methods using the disclosed adhesive composition.

30 Claims, No Drawings

MEDICAL ADHESIVES FOR QUICK RELEASE OF ANTIMICROBIALS

CROSS-REFERENCE TO RELATED APPLICATION

The present application is a 371 of International Application No. PCT/US2019/036771 which was published in English on Dec. 19, 2019, and claims the benefit of U.S. Provisional Patent Application No. 62/684,459 filed Jun. 13, 2018, both of which are incorporated herein by reference in their entireties.

FIELD

The present disclosure relates generally to adhesives particularly useful for the quick release of antimicrobial agents from medical dressings and drapes, resulting in the rapid onset of antimicrobial activity.

BACKGROUND

Adhesives, and particularly pressure sensitive adhesives, are routinely used in conjunction with a wide array of medical articles to attach or retain these articles to human skin. For example, hydrocolloid containing dressings and adhesive articles are commonly used in the treatment of wounds. In many instances, the hydrocolloid containing dressings and adhesive articles may comprise a variety of dressings, drapes including but not limited to surgical incise drapes, and sealing components that may be used in various medical applications. In some instances, the hydrocolloid containing dressings and adhesive articles may be used in negative pressure wound therapy (NPWT). In such treatment therapies, dressings, drapes, and sealing components are placed over a desired area of a patient's body, for example a wound area, to form a sealed area to be subjected to reduced pressure. Dressings and drapes may be provided with an adhesive coating along their underside for adhering and sealing the dressing or drape to the patient's skin.

In some cases, attempts have been made to use antimicrobial adhesives with such medical articles. However, there are several challenges associated with the incorporation of antimicrobial agents into adhesive compositions, and with the effective release of these agents from the adhesive. For example, adding antimicrobial agent to an adhesive typically impairs adhesion. Thus, in order to obtain sufficiently high antimicrobial efficacy and necessary adhesive properties, the coat weight of the adhesive must be increased. Although increased coat weight can yield higher antimicrobial concentration per surface area and promote maintenance of adequate adhesion, the increase in adhesive coat weight can also interfere with the stability or release of the antimicrobial agent from the adhesive if the adhesive component binds to or otherwise negatively interacts with the antimicrobial agent.

In addition, to obtain adequate antimicrobial efficacy of the medical adhesive article, high concentrations of antimicrobial agents can be required in conventional adhesive medical articles. This high concentration can tend to generate toxicity to the skin. It is therefore challenging for conventional antimicrobial adhesives to generate a high reduction of microbial activity without generating cytotoxic side effects.

In view of these challenges with the use of conventional medical adhesive technologies, the need therefore remains for improved adhesive compositions having enhanced antimicrobial agent release characteristics as well as other advantages.

SUMMARY

In one embodiment, the disclosure is to an adhesive composition. In some embodiments, the adhesive composition may comprise a silicone adhesive. In some embodiments, the silicone adhesive is an alcohol-functionalized silicone adhesive. In other embodiments, the silicone adhesive is a carboxyl-functionalized silicone adhesive. The adhesive composition may also comprise at least one phase-separated hydrophilic material. The adhesive composition may further comprise at least one bioactive compound. In other embodiments, the adhesive composition may comprise an acrylic adhesive. In some embodiments, the acrylic adhesive is an alcohol-functionalized acrylic adhesive. In other embodiments, the acrylic adhesive is a carboxyl-functionalized acrylic adhesive. The adhesive composition may also comprise at least one phase-separated hydrophilic material. The adhesive composition may further comprise at least one bioactive compound. In yet other embodiments, the adhesive composition may comprise at least one adhesive; at least one phase-separated hydrophilic material; and at least one bioactive compound. In many embodiments, the adhesive composition may comprise at least one adhesive of an alcohol-functionalized acrylic adhesive, a carboxyl-functionalized acrylic adhesive, an alcohol-functionalized silicone adhesive, and a carboxyl-functionalized silicone adhesive. In many embodiments, the concentration of the adhesive of the adhesive composition ranges from about 60 wt % to about 95 wt % wherein the adhesive is at least one adhesive of an alcohol-functionalized acrylic adhesive, a carboxyl-functionalized acrylic adhesive, an alcohol-functionalized silicone adhesive, and a carboxyl-functionalized silicone adhesive. In many embodiments, the adhesive composition further comprises a phase-separated hydrophilic material. In many embodiments, the concentration of the phase-separated hydrophilic material in the adhesive composition ranges from about 2 wt % to about 40 wt %. In many embodiments, the phase-separated hydrophilic material comprises silicon dioxide, zinc oxide, titanium dioxide, calcium carbonate, starches, crystalline cellulose, microcrystalline cellulose, carboxylmethyl cellulose, crospovidone, clay, or combinations thereof. The adhesive composition may also further comprise at least one bioactive compound. In most embodiments, the concentration of the bioactive compound in the adhesive composition ranges from about 1 wt % to about 10 wt %. In many embodiments, the bioactive compound is an antimicrobial agent. In some embodiments, the release rate of the bioactive compound into water is at least about 50 μg/cm' within 90 minutes of contact of the adhesive composition with water. In some embodiments, the release rate of the bioactive compound into water is at least about 75 $\mu g/cm^2$ within 90 minutes of contact of the adhesive composition with water. In some embodiments, the release rate of the bioactive compound into water is at least about 100 $\mu g/cm^2$ within 90 minutes of contact of the adhesive composition with water. In some embodiments, the release rate of the bioactive compound into water is at least about 120 $\mu g/cm^2$ within 90 minutes of contact of the adhesive composition with water. In some embodiments, the adhesive composition has antimicrobial activity resulting in at least a 4 log reduction in a *Pseudomonas aeruginosa, Staphylococcus epidermidis, Enterococcus faecalis* (TARE), *Enterobacter aerogenes, Escherichia coli,*

*Staphylococcus aureus*, or *Candida albicans* population within 90 minutes of contact of the adhesive composition with the population. In other embodiments, the adhesive composition has antimicrobial activity resulting in at least a 1 log reduction in an *Aspergillus brasilienis* population within 90 minutes of contact of the adhesive composition with the population. In other embodiments, the adhesive composition has antimicrobial activity resulting in at least a 0.1 log reduction in an *Aspergillus brasilienis* population within 90 minutes of contact of the adhesive composition with the population. In many embodiments, the adhesive composition has a grade 0 cytotoxicity. In some embodiments, the adhesive composition has a grade 1 cytotoxicity. In some embodiments, the adhesive composition has a grade 2 cytotoxicity. In many embodiments, the adhesive composition has a cytotoxicity grade of less than or equal to 2. In other embodiments, the adhesive composition has a Primary Irritation Index value of less than or equal to 2.

In another embodiment the disclosure relates to an adhesive product. The adhesive product comprises a substrate layer, and an adhesive layer disposed on at least a portion of a surface of the substrate layer. The adhesive layer comprises any of the disclosed adhesive compositions. In many embodiments, the substrate layer may comprise a polyethylene film, a polyurethane film, a polyvinylchloride film, a polyethylene foam, a polyurethane foam, a polyvinylchloride foam, nonwoven polyurethane, nonwoven elastomeric polyester, knitted fabric, woven fabric, or combinations thereof. In some embodiments, the substrate layer comprises a waterproof, flexible, non-adhesive film. In other embodiments, the adhesive product is configured for conformable topical application to biological skin. In many embodiments, the adhesive product is a pressure sensitive adhesive bandage, a wound covering, a medical dressing, a surgical dressing, a surgical drape, a surgical tape, or a medical tape.

In another embodiment, the disclosure is to a method for the release of at least one bioactive compound to a subject. The method comprises providing any of the disclosed adhesive products. The method further comprises contacting the adhesive layer of the adhesive product to a biological skin surface of the subject, thereby delivering the bioactive compound of the adhesive product to the subject. In some embodiments, the biological skin surface is proximate to a wound or surgical site of the subject. In many embodiments, the subject is human.

In another embodiment, the disclosure is to a method for producing an adhesive composition. The method comprises providing an adhesive of any of the disclosed adhesives herein, at least one phase-separated hydrophilic material, and at least one bioactive compound. In some embodiments, the adhesive is alcohol-functionalized. In other embodiments, the adhesive is carboxyl-functionalized. The method further comprises combining the adhesive, the phase-separated hydrophilic material(s), and the bioactive compound(s) to produce the adhesive composition.

DETAILED DESCRIPTION

The present disclosure generally relates to adhesive compositions that, when employed for example in medical applications, provide advantageous improvements, inter alia, in the release of desired bioactive compounds from the adhesive composition. It would be beneficial for an adhesive material applied to a target site to quickly deliver chemical treatments to the site. For example, it would be beneficial for medical adhesive products to rapidly supply antimicrobial agents to a wound or surgical site, quickly facilitating the onset of antimicrobial activity shortly after application of the adhesive product. The ability of adhesive medical products to quickly provide an antimicrobial effect can advantageously reduce the occurrence or severity of microbial infections, and can improve patient outcomes.

In certain applications, it is desirable that the adhesives achieve relatively high release rates and/or extents of release of antimicrobial agents incorporated in the adhesive. High release rates and/or extents of release of antimicrobial agents in relatively short time periods can be a prerequisite to using an adhesive in, for example, medical incise films or peripheral IV dressings.

There are challenges associated with balancing the above needs for an adhesive formulation to not inhibit bioactive compound release with further needs for the adhesive to meet requirements for dermal application. These requirements include good adhesion to skin, no to low toxicity to a patient, and minimal irritation caused by application of the medical adhesive product. As noted above, an increase in the amount of antimicrobial agent in an adhesive formulation typically results in a decrease in the adhesive properties of the formulation. Generally speaking, adhesive formulation characteristics that help to achieve some of these goals, however, are in opposition to other goals. It has been found difficult for an adhesive composition to simultaneously address each of these demands.

Disclosed herein are certain adhesive compositions that beneficially provide for a synergistic combination of both dermal application and the quick release of compounds, e.g., bioactive compounds such as antimicrobial agents, into a surrounding aqueous medium such as that of a wound or surgical site. In particular, it has been found that by utilizing alcohol-functionalized ("OH-functionalized") adhesives and carboxyl-functionalized ("COOH-functionalized") adhesives in the adhesive compositions described herein, the resulting adhesive composition can surprisingly release compounds at a faster rate and with a higher activity.

Also, it has been discovered that the use of particular phase-separated hydrophilic materials in the adhesive composition can surprisingly lead to the creation of micron-scale hydrophilic channels with the adhesive with minimal or no water absorption. These channels can also act to enhance the release of bioactive compounds from within the adhesive composition. Importantly, some of the phase-separated hydrophilic materials of the disclosed adhesive compositions also advantageously provide the adhesive with improved stability in various different sterilization procedures that can be used in preparing the adhesive for medical application. These sterilization procedures can include, for example, gamma radiation and ethylene oxide gas treatment. In certain aspects, the phase-separated hydrophilic materials are selected from silicon dioxide, zinc oxide, titanium dioxide, calcium carbonate, starches, crystalline cellulose, microcrystalline cellulose, carboxylmethyl cellulose, crospovidone, clay, or a combination thereof.

Adhesive Composition

In one embodiment, an adhesive composition is disclosed. The adhesive composition may include at least one adhesive, at least one phase-separated hydrophilic material, and at least one bioactive compound. In many embodiments, at least one adhesive may be an acrylic adhesive and/or a silicone adhesive. In many embodiments, the adhesive composition may also comprise at least one adhesive of an alcohol-functionalized acrylic adhesive, a carboxyl-functionalized acrylic adhesive, an alcohol-functionalized silicone adhesive, and a carboxyl-functionalized silicone adhesive. Additionally, at least one adhesive may be silicone, rubber, polyisobutylene (PIB), and a hybrid adhesive. The hybrid adhesive may be a hybrid comprising at least one silicone adhesive and/or at least one acrylic adhesive. In some embodiments, at least one adhesive may be a pressure sensitive adhesive.

In another embodiment, the adhesive composition may include: 1) at least one adhesive of an alcohol-functionalized acrylic adhesive, a carboxyl-functionalized acrylic adhesive, an alcohol-functionalized silicone adhesive, and a carboxyl-functionalized silicone adhesive, 2) at least one phase-separated hydrophilic material, and 3) at least one bioactive compound.

In certain aspects, at least one adhesive is an alcohol-functionalized adhesive. In some embodiments, the adhesive may comprise an acrylic adhesive, wherein the acrylic adhesive is an alcohol-functionalized acrylic adhesive. In other embodiments, the adhesive may comprise a silicone adhesive, wherein the silicone adhesive is an alcohol-functionalized silicone adhesive. In many embodiments, the adhesive composition may also comprise at least one adhesive of an alcohol-functionalized acrylic adhesive and an alcohol-functionalized silicone adhesive. In certain aspects, at least one adhesive is a carboxyl-functionalized adhesive. In some embodiments, the adhesive may comprise an acrylic adhesive, wherein the acrylic adhesive is a carboxyl-functionalized acrylic adhesive. In other embodiments, the adhesive may comprise a silicone adhesive, wherein the silicone adhesive is a carboxyl-functionalized silicone adhesive. In many embodiments, the adhesive composition may also comprise at least one adhesive of an alcohol-functionalized acrylic adhesive, a carboxyl-functionalized acrylic adhesive, an alcohol-functionalized silicone adhesive, and a carboxyl-functionalized silicone adhesive.

In many embodiments, the concentration of the adhesive ranges from about 60 wt % to about 95 wt % of the adhesive composition. In many embodiments, the concentration of at least one adhesive ranges from about 60 wt % to about 95 wt % of the adhesive composition. In other embodiments, the concentration of the adhesive ranges from about 75 wt % to about 90 wt % of the adhesive composition. Besides the adhesive, the adhesive composition also comprises at least one phase-separated hydrophilic material and at least one bioactive compound. The selection and concentration of these materials within the adhesive composition provide it with advantageous properties associated with the rapid release of the bioactive compound from the adhesive composition when contacted with water. This rapid release results in an increased bioactive compound release rate, particularly during the first 1-2 hours of adhesive application. The rapid release also results in the overall delivery of a greater percentage of the bioactive compound from within the composition, both during the initial hours of application, and during the overall application lifetime of the adhesive composition.

The alcohol-functionalized adhesive of the disclosed adhesive compositions may vary, as long as it contains alcohol-functionalization. In some embodiments, the alcohol-functionalized adhesive of the disclosed adhesive compositions may comprise alcohol-functionalized acrylic adhesive. In other embodiments, the alcohol-functionalized adhesive of the disclosed adhesive compositions may comprise alcohol-functionalized silicone adhesive. In yet other embodiments, the alcohol-functionalized adhesive of the disclosed adhesive compositions may comprise both alcohol-functionalized acrylic adhesive and alcohol-functionalized silicone adhesive. In some cases, the alcohol-functionalized adhesive can be selected to provide, for example, good skin adhesion characteristics, conformability to skin surfaces, and gentle release from a skin or wound site. The adhesive for use in the present subject matter can be an aqueous-based or a solvent-based adhesive. These adhesives may include one or more acrylate copolymers. These adhesives may also include one or more silicone polymers. These adhesives may also include homopolymers.

The carboxyl-functionalized adhesive of the disclosed adhesive compositions may vary, as long as it contains carboxyl-functionalization. In some embodiments, the carboxyl-functionalized adhesive of the disclosed adhesive compositions may comprise carboxyl-functionalized acrylic adhesive. In other embodiments, the carboxyl-functionalized adhesive of the disclosed adhesive compositions may comprise carboxyl-functionalized silicone adhesive. In yet other embodiments, the carboxyl-functionalized adhesive of the disclosed adhesive compositions may comprise both carboxyl-functionalized acrylic adhesive and carboxyl-functionalized silicone adhesive. In some cases, the carboxyl-functionalized adhesive can be selected to provide, for example, good skin adhesion characteristics, conformability to skin surfaces, and gentle release from a skin or wound site. The adhesive for use in the present subject matter can be an aqueous-based or a solvent-based adhesive. These adhesives may include one or more acrylate copolymers. These adhesives may also include one or more silicone polymers. These adhesives may also include homopolymers.

Further, the adhesive composition disclosed herein may also comprise both alcohol-functionalized adhesive and carboxyl-functionalized adhesives. In some embodiments, the adhesive may comprise at least one acrylic adhesive. In other embodiments, the adhesive may comprise at least one silicone adhesive. In some embodiments, the adhesive may comprise at least one acrylic adhesive and at least one silicone adhesive.

Useful acrylate copolymers may or may not be self-crosslinking and can be formed from at least two monomers. The monomers of the alcohol-functionalized acrylic adhesive can, for example, include hydroxyalkyl esters of acrylic or methacrylic acid in which the alkyl group comprises 2 to 4 carbon atoms, such as 2-hydroxyethyl acrylate, 2-hydroxyethyl methacrylate, 2-hydroxypropyl acrylate, 2-hydroxypropyl acrylate, and 2-hydroxypropyl methacrylate. The monomers of the alcohol-functionalized acrylic adhesive can include alkyl esters of acrylic or methacrylic acid in which the alkyl group of the ester comprises 4 to 18 carbon atoms, such as n-butyl acrylate or methacrylate, isopropyl acrylate or methacrylate, n-hexyl methacrylate, and 2-ethylhexyl acrylate. The monomers of the alcohol-functionalized acrylic adhesive can include α,β-unsaturated monocarboxylic or dicarboxylic acids, their anhydrides, and their alkyl or alkenyl esters in which the alkyl group contains from 1 to 3 carbon atoms and the alkenyl group contains from 2 to 5 carbon atoms, such as acrylic acid, itaconic acid, maleic acid, maleic anhydride, alkyl methacrylate, and the diethyl esters of fumaric or maleic acid. The monomers of the alcohol-functionalized acrylic adhesive can include vinyl monomers, such as vinyl acetate, acrylonitrile, vinyl propionate, vinylpyrrolidone, and styrene. The monomers of the alcohol-functionalized acrylic adhesive can include monomers containing a functional group selected from amido, amino, and epoxy groups, for example, acrylamide, N-butylacrylamide, alkylaminoalkyl and aminoalkyl derivatives of acrylic or methacrylic acid, such as aminoethyl acrylate, aminoethyl methacrylate and 2-(dimethylamino) ethyl methacrylate, glycidyl methacrylate, and glycidyl acrylate. The monomers of the alcohol-functionalized acrylic adhesive can include alkoxyalkyl esters of acrylic or methacrylic acid, for example methoxyethyl acrylates or methacrylates, butoxyethyl acrylates or methacrylates. methoxypropylene glycol acrylates or methacrylates, and methoxypolyethylene glycol acrylates or methacrylates. The monomers of the alcohol-functionalized acrylic adhesive can include, but are not limited to, hexamethylene glycol dimethacrylate. The monomers of the carboxyl-functionalized acrylic adhesive can include, but are not limited to, acrylic acid, methacrylic acid, and maleic acid.

In cases where these copolymers are crosslinkable or at least partially crosslinked, they may also contain a crosslinking agent selected from those generally used by those skilled in the art, for example, organic peroxides, polyisocyanates, chelates or metals such as titanium or aluminum, or metal acetylacetonates, such as those of zinc, magnesium, and aluminum.

These adhesive acrylate copolymers can take the form of solutions in a solvent system including a single organic solvent or a mixture of several solvents, which contain about 25% to about 55% by weight (wt) copolymers. Examples of suitable solvents include aromatic solvents such as toluene, xylene, and other solvents. Suitable aliphatic solvents may include, but are not limited to, esters such as ethyl acetate, propyl acetate, isopropyl acetate, and butyl acetate; ketones such as methyl ethyl ketone, and acetone; and aliphatic hydrocarbons such as heptanes, hexane, and pentane. Other suitable solvents may also include alcohols such as, but not limited to, methanol, ethanol, and isopropyl alcohol.

In many embodiments, useful silicone adhesives comprise silicone-based monomers. Examples of suitable commercial silicone-based adhesives are described herein. These products are exemplary and are not meant to limit the scope of the silicone adhesives.

Where the monomer is a silicone-based monomer, the monomer may be a single polymer species or a mixture of two or more polymers, as long as at least one of the polymers is a silicone-based polymer. In many embodiments, the silicone adhesive has a siloxane backbone. In many embodiments, the silicone adhesive is comprised of polydimethylsiloxane (PDMS). For the silicone PSA, weight average molecular weight (Mw), Mw distribution, MQ resin type, and other polymer compositional factors may affect the properties of the silicone adhesive.

The silicone-based monomer of the silicone-based polymer may comprise, but are not limited to, siloxanes, silanes, silatrane glycols, and mixtures thereof. Other suitable silicone-based monomers include, 1,4-Bis[dimethyl[2-(5-norbornen-2-yl)ethyl]silyl]benzene; 1,3-Dicyclohexyl-1,1,3,3-tetrakis(dimethylsilyloxy)disiloxane; 1,3-Dicyclohexyl-1,1,3,3-tetrakis(dimethylvinylsilyloxy)disiloxane; 1,3-Dicyclohexyl-1,1,3,3-tetrakis[(norbornen-2-yl)ethyldimethylsilyloxy]disiloxane; 1,3-Divinyltetramethyldisiloxane; 1,1,3,3,5,5-Hexamethyl-1,5-bis[2-(5-norbornen-2-yl)ethyl]trisiloxane; 1,1,3,3-Tetramethyl-1,3-bis[2-(5-norbornen-2-yl)ethyl]disiloxane; 2,4,6,8-Tetramethyl-2,4,6,8-tetravinylcyclotetrasiloxane; N-[3-(Trimethoxysilyl)propyl]-N'-(4-vinylbenzyl)ethylenediamine; 3-[Tris(trimethylsiloxy)silyl]propyl vinyl carbamate; and mixtures thereof. Combinations of these monomers may be polymerized to form the silicone-based adhesive.

Suitable commercially available silicone-based products, e.g., that contain silicone polymer, include but are not limited to, products from KRT 009 (Shin Etsu), PSA 6574 (Momentive), Q2-7735 (Dow Corning), DC 282 (Dow Corning), DC 280A (Dow Corning), DC 7957 (Dow Corning), DC 7956 (Dow Corning), BioPSA (Dow Corning), Q2-7406 (Dow Corning), KRT 026 (Shin Etsu), KRT 002 (Shin Etsu), KRT 006 (Shin Etsu), KRT 003 (Shin Etsu), KR 3700 (Shin Etsu), KCT 7771 (Shin Etsu), KR 100 (Shin Etsu), PSA 518 (Momentive), PSA 915 (Momentive), PSA 595 (Momentive), PSA 610e (Momentive), Bluestar PSA 400, and PSA 418 (Bluestar).

It will be appreciated that the present subject matter is not limited to any particular silicone polymer component, and includes a wide array of such components.

Further, the adhesive composition described herein may comprise at least one adhesive that is a pressure-sensitive adhesive (PSA), including any pressure sensitive adhesive that is capable of adhering to mammalian skin and that is free of ingredients known to cause undue irritation or toxicity to mammals. One well known means of identifying PSAs is the Dahlquist criterion. This criterion defines a PSA as an adhesive having a 1 second creep compliance of greater than $1\times10^{-6}$ $cm^2$/dyne as described in Handbook of PSA Technology, Donatas Satas (Ed.), 2$^{nd}$ Edition, p. 172, Van Nostrand Reinhold, New York, N.Y., 1989. Alternatively, since modulus is, to a first approximation, the inverse of creep compliance, PSAs may be defined as adhesives having a Young's modulus of less than $1\times10^{6}$ dynes/$cm^2$. Another well-known means of identifying a PSA is that it is aggressively and permanently tacky at room temperature and firmly adheres to a variety of dissimilar surfaces upon mere contact without the need of more than finger or hand pressure, and which may be removed from smooth surfaces without leaving a residue as described in Glossary of Terms Used in the Pressure Sensitive Tape Industry provided by the Pressure Sensitive Tape Council, 1996. Another suitable definition of a suitable PSA is that it preferably has a room temperature storage modulus within the area defined by the following points as plotted on a graph of modulus versus frequency at 25° C.: a range of moduli from approximately $2\times10^{5}$ to $4\times10^{5}$ dynes/$cm^2$ at a frequency of approximately 0.1 radians/sec (0.017 Hz), and a range of moduli from approximately $2\times10^{6}$ to $8\times10^{6}$ dynes/$cm^2$ at a frequency of approximately 100 radians/sec (17 Hz) (for example see FIGS. 8-16 on p. 173 of Handbook of PSA Technology (Donatas Satas, Ed.), 2$^{nd}$ Edition, Van Nostrand Rheinhold, N.Y., 1989). Any of these methods of identifying a PSA may be used to identify suitable PSAs for use in accordance with the present subject matter.

Additionally, at least one adhesive may be a hybrid adhesive. The hybrid adhesive may be a hybrid comprising at least one silicone adhesive and/or at least one acrylic adhesive.

In some embodiments, the adhesive may not be tacky at room temperature, but may be a tacky PSA after the addition of a tackifier.

The adhesive can include a wide array of additive materials. Additives, such as certain pigments, ultraviolet light absorbers, ultraviolet stabilizers, antioxidants, post curing agents, and the like can be blended into the adhesive to modify its properties.

The combined concentration of at least one adhesive of an alcohol-functionalized acrylic adhesive, an alcohol-functionalized silicone adhesive, a carboxyl-functionalized acrylic adhesive, and a carboxyl-functionalized silicone adhesive in the adhesive composition described herein can, for example, range from about 60 wt % to about 95 wt %, e.g., from about 70 wt % to about 85 wt %, from about 72.5 wt % to about 87.5 wt %, from about 75 wt % to about 90 wt %, from about 77.5 wt % to about 92.5 wt %, about 80 wt % to about 90 wt %, or from about 80 wt % to about 95 wt %.

In terms of upper limits, the concentration of the alcohol-functionalized acrylic adhesive(s) can be less than about 95 wt %, less than about 92.5 wt %, less than about 90 wt %, less than about 87.5 wt %, less than about 85 wt %, less than about 82.5 wt %, less than about 80 wt %, less than about 77.5 wt %, less than about 75 wt %, or less than about 72.5 wt %. In terms of lower limits, the concentration of the alcohol-functionalized acrylic adhesive(s) can be eat least about 60 wt %, e.g., at least about 65 wt %, at least about 70 wt %, at least about 72.5 wt %, at least about 75 wt %, at least about 77.5 wt %, at least about 80 wt %, at least about 82.5 wt %, at least about 85 wt %, at least about 87.5 wt %, at least about 90 wt %, or at least about 92.5 wt %. Higher concentrations, e.g., at least about 95 wt %, and lower concentrations, e.g., less than about 60 wt %, are also contemplated.

In terms of upper limits, the concentration of the alcohol-functionalized silicone adhesive(s) can be less than about 95 wt %, less than about 92.5 wt %, less than about 90 wt %, less than about 87.5 wt %, less than about 85 wt %, less than about 82.5 wt %, less than about 80 wt %, less than about 77.5 wt %, less than about 75 wt %, or less than about 72.5 wt %. In terms of lower limits, the concentration of the alcohol-functionalized silicone adhesive(s) can be eat least about 60 wt %, e.g., at least about 65 wt %, at least about 70 wt %, at least about 72.5 wt %, at least about 75 wt %, at least about 77.5 wt %, at least about 80 wt %, at least about 82.5 wt %, at least about 85 wt %, at least about 87.5 wt %, at least about 90 wt %, or at least about 92.5 wt %. Higher concentrations, e.g., at least about 95 wt %, and lower concentrations, e.g., less than about 60 wt %, are also contemplated.

In terms of upper limits, the concentration of the carboxyl-functionalized acrylic adhesive(s) can be less than about 95 wt %, less than about 92.5 wt %, less than about 90 wt %, less than about 87.5 wt %, less than about 85 wt %, less than about 82.5 wt %, less than about 80 wt %, less than about 77.5 wt %, less than about 75 wt %, or less than about 72.5 wt %. In terms of lower limits, the concentration of the carboxyl-functionalized acrylic adhesive(s) can be eat least about 60 wt %, e.g., at least about 65 wt %, at least about 70 wt %, at least about 72.5 wt %, at least about 75 wt %, at least about 77.5 wt %, at least about 80 wt %, at least about 82.5 wt %, at least about 85 wt %, at least about 87.5 wt %, at least about 90 wt %, or at least about 92.5 wt %. Higher concentrations, e.g., at least about 95 wt %, and lower concentrations, e.g., less than about 60 wt %, are also contemplated.

In terms of upper limits, the concentration of the carboxyl-functionalized silicone adhesive(s) can be less than about 95 wt %, less than about 92.5 wt %, less than about 90 wt %, less than about 87.5 wt %, less than about 85 wt %, less than about 82.5 wt %, less than about 80 wt %, less than about 77.5 wt %, less than about 75 wt %, or less than about 72.5 wt %. In terms of lower limits, the concentration of the carboxyl-functionalized silicone adhesive(s) can be eat least about 60 wt %, e.g., at least about 65 wt %, at least about 70 wt %, at least about 72.5 wt %, at least about 75 wt %, at least about 77.5 wt %, at least about 80 wt %, at least about 82.5 wt %, at least about 85 wt %, at least about 87.5 wt %, at least about 90 wt %, or at least about 92.5 wt %. Higher concentrations, e.g., at least about 95 wt %, and lower concentrations, e.g., less than about 60 wt %, are also contemplated.

Phase-Separated Hydrophilic Material

The adhesive composition can include one or more phase-separated hydrophilic materials. The phase-separated hydrophilic materials are not dissolved in the adhesive but are instead phase-separated from the adhesive. Phase-separated hydrophilic materials may be agents added to compositions to promote the breakup or disintegration of the composition into smaller fragments in an aqueous environment, thereby increasing the available surface area and promoting a more rapid release of one or more hydrophilic active agents or substances contained in the composition. Further, phase-separated hydrophilic materials may allow water or other solvents or liquids to move into the matrix to extract one or more active agents more efficiently. In many embodiments, the phase-separated hydrophilic materials may be solid, plasma, liquid, gel, or some other form. In certain aspects, the phase-separated hydrophilic material of the disclosed adhesive composition is a medical or pharmaceutical grade material. In certain aspects, the phase-separated hydrophilic material is crospovidone. In other aspects, the phase-separated hydrophilic material is microcrystalline cellulose. In certain aspects, the phase-separated hydrophilic material is clay. In certain aspects, the phase-separated hydrophilic material is silicon dioxide. In other embodiments, the phase-separated hydrophilic material is silicon dioxide, zinc oxide, titanium dioxide, calcium carbonate, starches, crystalline cellulose, microcrystalline cellulose, crospovidone, clay, or a combination thereof.

For the adhesive composition described herein, the use of the disclosed phase-separated hydrophilic material unexpectedly provides at least some of the described advantages when used as a partial or complete replacement for cellulose phase-separated hydrophilic materials of conventional medical adhesives.

In certain aspects, the concentration of microcrystalline cellulose in the adhesive composition is less than about 40 wt %, e.g., less than about 35 wt %, less than about 30 wt %, less than about 25 wt %, less than about 20 wt %, less than about 15 wt %, less than about 10 wt %, less than about 6.4 wt %, less than about 4 wt %, less than about 2.5 wt %, less than about 1.6 wt %, less than about 1 wt %, less than about 0.63 wt %, less than about 0.4 wt %, less than about 0.25 wt %, less about 0.15 wt %, or less than about 0.1 wt %. The concentration of microcrystalline cellulose can, for example, range from about 0.1 wt % to about 1.6 wt %, from about 0.16 wt % to about 2.5 wt %, from about 0.25 wt % to about 4 wt %, from about 0.4 wt % to about 6.3 wt %, or from about 0.63 wt % to about 10 wt %. In other embodiments, the concentration of microcrystalline cellulose can, for example, range from about 0.1 wt % to about 40 wt %, from about 0.16 wt % to about 35 wt %, from about 0.25 wt % to about 30 wt %, from about 0.4 wt % to about 25 wt %, from about 0.5 wt % to about 20 wt %, from about 0.5 wt % to about 15 wt %, or from about 0.63 wt % to about 10 wt %.

The combined concentration of the one or more phase-separated hydrophilic materials in the adhesive composition can, for example, range from about 2 wt % to about 40 wt %, e.g., from about 2 wt % to about 35 wt %, from about 2 wt % to about 30 wt %, from about 2 wt % to about 25 wt %, from 2 wt % to 20 wt %, from 2 wt % to about 15 wt %, from about 2 wt % to about 12.8 wt %, from about 3.8 wt % to about 14.6 wt %, from about 5.6 wt % to about 16.4 wt %, from about 7 wt % to about 15 wt %; from about 7.4 wt % to about 18.2 wt %, or from about 9.2 wt % to about 20 wt %. In terms of upper limits, the phase-separated hydrophilic material concentration can be less than about 40 wt %, e.g., less than about 35 wt %, less than about 30 wt %, less than about 25 wt %, less than about 20 wt %, less than about 18.2 wt %, less than about 16.4 wt %, less than about 14.6 wt %, less than about 12.8 wt %, less than about 11 wt %, less than about 9.2 wt %, less than about 7.4 wt %, less than about 5.6 wt %, or less than about 3.8 wt %. In terms of lower limits, the phase-separated hydrophilic material concentration can be at least about 2 wt %, e.g., at least about 3.8 wt %, at least about 5.6 wt %, at least about 7.4 wt %, at least about 9.2 wt %, at least about 11 wt %, at least about 12.8 wt %, at least about 14.6 wt %, at least about 16.4 wt %, or at least about 18.2 wt %. Higher concentrations, e.g., at least about 20 wt %, 30 wt %, and 40 wt %, and lower concentrations, e.g., less than about 2 wt %, are also contemplated.

Generally, the phase-separated hydrophilic material(s) are uniformly dispersed within the composition but not dissolved within the composition. However, the present subject matter contemplates the use of non-uniform dispersions of the phase-separated hydrophilic material(s). For example, for certain applications it may be advantageous to provide a relatively high concentration of phase-separated hydrophilic material(s) along or proximate to a face of the adhesive layer, and a lower concentration of phase-separated hydrophilic material(s) within other regions spaced from the contacting face of the adhesive. Adhesive layers having concentration gradients of phase-separated hydrophilic materials within the layer, such as across a thickness of the layer, are also included in the present subject matter.

Bioactive Compound

As used herein, the term "bioactive" refers to a compound having a physiological effect on a biological system or subject as compared to a biological system or subject not exposed to the compound. The bioactive compound of the present disclosure can be an antibacterial agent, an antifungal agent, an analgesic agent, a tissue healant agent, a local anesthetic agent, an antibleeding agent, an enzyme, or a vasoconstrictor. The bioactive compound can be pharmaceutically active components such as, for example, an anti-inflammatory agent, analgesic agent, anesthetic, other pharmaceutically acceptable compound, or combinations thereof. The bioactive compound can be included in the adhesive composition in a pharmaceutically effective amount.

Examples of bioactive compounds include anionic agents such as those selected from antibacterials including fusidic acid, pseudomonic acid, and Ceftriaxone (Rocephin); antifungals including nafcillin, Nystatin, and undecylenic acid; analge sics including salicylic acid, salicylsulfonic acid, and nicotinic acid; and antibleeding agents including adenosine diphosphate. Further examples of bioactive compounds include cationic agents such as those selected from antibacterials including chlorhexidine, Bacitracin, Chlortetracycline, Gentamycin, Kanamycin, Neomycin B, Polymyxin B, Streptomycin, and Tetracycline; antifungals including Amphotericin B, ClotrimaZole, and MiconaZole; tissue healants including cysteine, glycine and threonine; local anesthetics such as Lidocaine; enzymes including trypsin, Streptokinase, plasmin (Fibrinolysin), and Streptodornase; deoxyribonuclease; and cationic vasoconstrictors including epinephrine and serotonin. Such biologically active agents can be used in the form of their salts. One or more bioactive compounds can be combined in the adhesive compositions of the present disclosure.

In certain aspects, the bioactive compound comprises an antimicrobial agent. As used herein. the terms "antimicrobial" and "inhibiting microbial growth" refer to the killing of, as well as the inhibition of or control of, the growth of bacteria, yeasts. fungi, and algae Enhancement of antimicrobial efficacy refers to increasing the rate of kill and/or decreasing the amount of necessary antimicrobial agent to achieve antimicrobial control.

Non-limiting examples of antimicrobial agents include diiodomethyl-para-tolylsulfone (DIMTS, Amical®), ortho-phenylphenol (OPP), sodium pyrithione (NaPT), zinc pyrithione (ZPT), 3-iodo-2-propynylbutylcarbamate (IPBC), 2-methyl-4-isothiazolin-3-one (MIT), 1,2-benzisothiazolin-3-one (BIT), 2-n-octyl-4-isothiazolin-3-one (OIT), 1-(3-chloroallyl)-3,5,7-triaza-1-azoniaadamantane chloride (CTAC. Dowicil 200), 2-(4-thiazolyl)-benzimidazole (TBZ, thiabendazole), β-bromo-β-nitrostyrene (BNS), 2,4,4'-trichloro-2-hydroxyphenyl ether (Triclosan), chloroxylenol (PCMX), chlorocresol (PCMC), para-tert-amylphenol (PTAP), N-(4-chlorophenyl)-N'-(3.4-dichlorophenyl)-urea (Trichlocarban), para-hydroxybenzoic acid esters (parabens), and mixtures thereof. A partial listing of antimicrobial agents may include, but are not limited to, DIMTS, OPP, NaPT, ZPT, IPBC, BIT, and OIT. In certain embodiments the antimicrobial agent is a bis-biguanide salt and particularly chlorhexidine or a chlorhexidine salt thereof. In some embodiments, the chlorhexidine salt may comprise chlorhexidine digluconate.

Non-volatile, water-soluble antimicrobial agents include natural components including botanical compounds such as aloe, acids such as anisic acid, hydroxy acids such as lactic acid, polypeptides such as N-cocoyl-L-arginine ethyl ether DL-pyrrolidone carboxylate CAE, enzymes such as lactoperoxidase, polysaccharides such as chitosan, and proteins such as ionic lysostaphin; synthetic components including metal salts such as copper acetate and silver sulfadiazine, phenol derivatives such as phenoxyethanol, sulfur-containing compounds such as mafenide acetate, surfactants such as Nonoxynol-9, aminoglycosides such as streptomycin, iodine complexes such as povidone-iodine, hydric solvents such as benzyl alcohol, alkyl guanidines such as dodecylguanidine hydrochloride (DGH), anionic polymers such as polystyrene sulfonate, cationic polymers such as polytrimethoxysilyl propyldimethyloctadecyl ammonium chloride (AEM 5700TM), and cationic nitrogen-containing organic compounds such as bis-biguanide salts and quaternary ammonium salts such as poly[(dimethylimino)-2-butene-1.4-diyl-chloride] and [4-tris(2-hydroxyethyl)ammonio]-2-butenyl-w-[tris(2-hydroxyethyl)ammonio]dichloride available as Polyquatemium-1. In certain embodiments. it is contemplated that in addition to the metal salts noted herein, other metal salts with antimicrobial metallic ions, for example mercury, could be used and furthermore that nonmetallic ions having antibacterial properties could also be utilized. Additional examples of other quaternary ammonium compounds which can be used as antimicrobial agents include but are not limited to Cetremide, Domiphen Bromide, polymeric quaternaries, and iodophores such as Povidone Iodine.

Bis-biguanide salts include hexamethylene biguanide hydrochloride (available as Vantocil 1139), polyhexamethylene biguanide hydrochloride (also known as PHMB, available as Cosmocil CQ®), bis-biguanide alkanes, and mixtures thereof. In some embodiments, the bis-biguanide salt is 1.1'-hexamethylene bis(5-(p-chlorophenyl)biguanide) salt commonly known as chlorhexidine salt. This form includes chlorhexidine acetate, chlorhexidine diacetate, chlorhexidine dihydrochloride, chlorhexidine diphosphanilate, or chlorhexidine digluconate, which mainly differ in their solubility profiles in various solvents and in their application. In certain aspects, the antimicrobial agent of the adhesive composition is chlorhexidine digluconate, i.e., chlorhexidine gluconate (CHG). The CHG can be present in an amount ranging from about 0.01%, and more particularly from about 0.5%, to about 85% by weight (wt) of total solids, even more particularly from about 1.0% to about 75.0% by weight (wt) of total solids, and most particularly from about 1.0% to about 10.0% by weight (wt) of total solids.

The concentration of the bioactive compound in the adhesive composition can, for example, range from about 1 wt % to about 10 wt %, e.g., from about 2 wt % to about 6.8 wt %, from about 2.8 wt % to about 7.6 wt %, from about 3.6 wt % to about 8.4 wt %, from about 4.4 wt % to about 9.2 wt %, or from about 5.2 wt % to about 10 wt %. In terms of upper limits, the phase-separated hydrophilic material concentration can be less than about 10 wt %, e.g., less than about 9.2 wt %, less than about 8.4 wt %, less than about 7.6 wt %, less than about 6.8 wt %, less than about 6 wt %, less than about 5.2 wt %, less than about 4.4 wt %, less than about 3.6 wt %, or less than about 2.8 wt %. In terms of lower limits, the phase-separated hydrophilic material concentration can be at least about 2 wt %, e.g., at least about 2.8 wt %, at least about 3.6 wt %, at least about 4.4 wt %, at least about 5.2 wt %, at least about 6 wt %, at least about 6.8 wt %, at least about 7.6 wt %, at least about 8.4 wt %, or at least about 9.2 wt %. Higher concentrations, e.g., at least about 10 wt %, and lower concentrations, e.g., less than about 2 wt %, are also contemplated.

Performance Characteristics

In certain aspects, within 90 minutes of contact of the adhesive composition with water, the adhesive composition has a cumulative release rate of the bioactive compound into the water that is at least about 50 $\mu g/cm^2$, e.g., at least about 75 $\mu g/cm^2$, at least about 80 $\mu g/cm^2$, at least about 96 $\mu g/cm^2$, at least about 100 $\mu g/cm^2$, at least about 112 $\mu g/cm^2$, at least about 128 $\mu g/cm^2$, at least about 144 $\mu g/cm^2$, at least about 160 $\mu g/cm^2$, at least about 176 $\mu g/cm^2$, at least about 192 $\mu g/cm^2$, at least about 208 $\mu g/cm^2$, or at least about 240 $\mu g/cm^2$. The release rate of the bioactive compound into water within 90 minutes of contact can, for example, range from about 50 $\mu g/cm^2$ to about 176 $\mu g/cm^2$, from about 96 $\mu g/cm^2$ to about 192 $\mu g/cm^2$, from about 112 $\mu g/cm^2$ to about 208 $\mu g/cm^2$, from about 128 $\mu g/cm^2$ to about 224 $\mu g/cm^2$, or from about 144 $\mu g/cm^2$ to about 240 $\mu g/cm^2$.

In certain aspects, within 90 minutes of contact of the adhesive composition with water, the percentage of the adhesive composition bioactive compound that is released into the water is at least about 25%, at least about 31%, at least about 37%, at least about 43%, at least about 49%, at least about 55%, at least about 61%, at least about 67%, at least about 73%, at least about 79%, or at least about 85%. The percentage of bioactive compound released into water within 90 minutes of contact can, for example, range from about 25% to about 61%, from about 31% to about 67%, from about 37% to about 73%, from about 43% to about 79%, or from about 49% to about 85%.

In some embodiments, the adhesive compositions exhibit antimicrobial efficacy against a broad spectrum of microbes, including but not limited to gram-positive bacteria, gram-negative bacteria, yeasts, fungi, and other microbes. Non-limiting examples may include gram-positive bacteria such as *Propionibacterium acnes, Streptococcus pyogenes, Staphylococcus epidermidis, Staphylococcus aureus, Enterococcus faecalis*, and *Enterococcus faecium*, Non-limiting examples may include gram negative bacteria such as *Burkholderia cepacia, Proteus mirabilis*, Enterobacteriaceae/3-lactamases, *Acinetobacter baumannii, Serratia marcescens, Escherichia coli, Enterobacter aerogenes, Klebsiella pneumonia*, and *Pseudomonas aeruginosa*. Other examples may include clinical isolates such as methicillin-resistant *Staphylococcus aureus* (MRSA), Carbapenem resistant *Klebsiella pneumonia* (CRE), and vancomycin-resistant *Enterococcus faecium* (VRE). The above noted bacteria can typically be found in a hospital environment. Additional non-limiting examples of additional microorganisms to which the present subject matter is directed may include *Candida albicans, Candida parapsilosis*, and *Aspergillus brasiliensiss*.

The adhesive composition can be effective in preventing or reducing the severity of infections by bacteria such as *Pseudomonas aeruginosa*. *P. aeruginosa* is a Gram-negative, rod-shaped bacterium associated with serious illnesses including hospital-acquired infections such as ventilator-associated pneumonia and various sepsis syndromes. Because it thrives on moist surfaces, *P. aeruginosa* can also be found on and in medical equipment, including catheters, causing cross-infections in hospitals and clinics. One measure of the efficacy of an antimicrobial treatment is the reduction of the number of viable microorganisms in a test population, e.g., a *P. aeruginosa* population, within a period of time as a result of application of the treatment. This reduction in microorganism viability can be expressed in terms of log reduction, wherein a log reduction of 1 indicates a $10^{-1}$, or 10%, probability that an individual microorganism of the test population remains viable and nonsterile. The log reduction of a microbial population in response to an antimicrobial agent can be measured according to, for example, the standard protocol ASTM E2315-16. In certain aspects, within 90 minutes of contact of the adhesive composition with a population of *P. aeruginosa*, the adhesive composition causes a log reduction in the *P. aeruginosa* population that is at least about 4, e.g., at least about 4.2, at least about 4.4, at least about 4.6, at least about 4.8, at least about 5, at least about 5.2, at least about 5.4, at least about 5.6, or at least about 5.8. The log reduction of the *P. aeruginosa* population within 90 minutes of contact can, for example, range from about 4 to about 5.2, from about 4.2 to about 5.4, from about 4.4 to about 5.6, from about 4.6 to about 5.8, or from about 4.8 to about 6.

The adhesive composition can be effective in preventing or reducing the severity of infections by bacteria such as *Escherichia coli*. *E. coli* is a Gram-negative, facultatively anaerobic, rod-shaped, coliform bacterium, some virulent strains of which can cause gastroenteritis, urinary tract infections, neonatal meningitis, hemorrhagic colitis, and Crohn's disease. In certain aspects, within 90 minutes of contact of the adhesive composition with a population of *E. coli*, the adhesive composition causes a log reduction in the *E. coli* population that is at least about 4, e.g., at least about 4.2, at least about 4.4, at least about 4.6, at least about 4.8, at least about 5, at least about 5.2, at least about 5.4, at least about 5.6, or at least about 5.8. The log reduction of the *E. coli* population within 90 minutes of contact can, for example, range from about 4 to about 5.2, from about 4.2 to about 5.4, from about 4.4 to about 5.6, from about 4.6 to about 5.8, or from about 4.8 to about 6.

The adhesive composition can be effective in preventing or reducing the severity of infections by bacteria such as *Staphylococcus aureus*. *S. aureus* is a common cause of a range of illnesses, from minor skin infections, such as pimples, impetigo, boils, cellulitis, folliculitis, carbuncles, scalded skin syndrome, and abscesses, to life-threatening diseases such as pneumonia, meningitis, osteomyelitis, endocarditis, toxic shock syndrome, bacteremia, and sepsis. *S. aureus* is one of the most common causes of hospital-acquired infections and is often the cause of wound infections following surgery. In certain aspects, within 90 minutes of contact of the adhesive composition with a population of *S. aureus*, the adhesive composition causes a log reduction in the *S. aureus* population that is at least about 4, e.g., at least about 4.2, at least about 4.4, at least about 4.6, at least about 4.8, at least about 5, at least about 5.2, at least about 5.4, at least about 5.6, or at least about 5.8. The log reduction of the *S. aureus* population within 90 minutes of contact can, for example, range from about 4 to about 5.2, from about 4.2 to about 5.4, from about 4.4 to about 5.6, from about 4.6 to about 5.8, or from about 4.8 to about 6.

The adhesive composition can be effective in preventing or reducing the severity of infections by yeast such as *Candida albicans, Candida tropicalis, Candida parapsilosis*, or *Candida glabrata. C. albicans* is a pathogenic yeast that is a common member of the human gut flora. Individuals at particular risk of *C. albicans* infections are those who are immunocompromised, or those who have recently undergone surgery, a transplant, or are in an Intensive Care Unit (ICU). In certain aspects, within 90 minutes of contact of the adhesive composition with a population of *C. albicans*, the adhesive composition causes a log reduction in the *C. albicans* population that is at least about 4, e.g., at least about 4.2, at least about 4.4, at least about 4.6, at least about 4.8, at least about 5, at least about 5.2, at least about 5.4, at least about 5.6, or at least about 5.8. The log reduction of the *C. albicans* population within 90 minutes of contact can, for example, range from about 4 to about 5.2, from about 4.2 to about 5.4, from about 4.4 to about 5.6, from about 4.6 to about 5.8, or from about 4.8 to about 6.

The adhesive composition can be effective in preventing or reducing the severity of infections by fungal molds such as *Aspergillus brasiliensis, Aspergillus tubingensis, Aspergillus foetidus, Aspergillus carbonarius*, or *Aspergillus awamori. A. brasiliensis* is a common cause of fungal infections of the lung and ear. In certain aspects, within 90 minutes of contact of the adhesive composition with a population of *Pseudomonas aeriginosa*, the adhesive composition causes a log reduction in the *P. aeriginosa* population that is at least about 0.1, e.g., at least about 0.2, at least about 0.3, at least about 0.5, at least about 1.0, at least about 1.5, at least about 2.0, at least about 2.2, at least about 2.4, at least about 2.6, at least about 2.8, at least about 3, at least about 3.2, at least about 3.4, at least about 3.6, or at least about 3.8. The log reduction of the P. aeriginosa population within 90 minutes of contact can, for example, range from about 0.1 to about 3.4, from about 0.5 to about 3.4, from about 1.0 to about 3.4, from about 1.5 to about 3.4, from about 2.0 to about 3.4, from about 2.2 to about 3.4, from about 2.4 to about 3.6, from about 2.6 to about 3.8, or from about 2.8 to about 4.

When an adhesive is to be used in the treatment of patients, it can be advantageous for the adhesive to have low to minimal cytotoxicity. The cytotoxicity of a material can be measured according to, for example, the standard protocol ISO 10993-5:2009. Generally, materials having a cytotoxicity grade of 4 are classified as having severe reactivity, a cytotoxicity grade of 3 are classified as having moderate reactivity, a cytotoxicity grade of 2 are classified as having mild reactivity, a cytotoxicity grade of 1 as having slight reactivity, and a cytotoxicity grade of 0 as having no reactivity. In certain aspects, the adhesive composition of the present disclosure has less than a grade 3 cytotoxicity. In certain aspects, the adhesive composition of the present disclosure has a grade 2 cytotoxicity. In certain aspects, the adhesive composition has a grade 1 cytotoxicity. In certain aspects, the adhesive composition has a grade 0 cytotoxicity. In many embodiments, the adhesive composition described herein has a cytotoxicity grade of less than or equal to 2. In many embodiments, the adhesive composition described herein has a cytotoxicity grade of less than 2.

It can further be advantageous for an adhesive intended for dermal application to produce low to minimal skin irritation. The skin irritation caused by a material can be measured according to, for example, standard protocol ISO 10993-10:2010. Generally, materials having Primary Irritation index values between 5 and 8 are classified are severe irritants, between 2 and 5 are classified as moderate irritants, between 0.5 and 2 are classified as mild irritants, and between 0 and 0.5 are classified as minimal irritants or non-irritants. In certain aspects, the disclosed adhesive composition has a Primary Irritation Index value that is less than 2, e.g., less than 1.85, less than 1.65, less than 1.5, less than 1.3, less than 1.15, less than 1, less than 0.8, less than 0.65, less than 0.45, or less than 0.3. The Primary Irritation Index value of the adhesive composition can, for example, range from 0.3 to 1.3, from 0.45 to 1.5, from 0.65 to 1.65, from 0.8 to 1.85, or from 1 to 2.

Adhesive Products

Also provided are adhesive products using the disclosed adhesive composition. The adhesive products include a substrate layer and an adhesive layer disposed on at least a portion of a surface of the substrate layer, wherein the adhesive layer includes the disclosed adhesive composition. In certain aspects, the adhesive product is configured for conformable topical application to biological skin. In some embodiments, the biological skin surface is proximate to a wound or surgical site of the subject. As used herein, the term "subject" refers to animals such as mammals, including, but not limited to, primates, cows, sheep, goats, horses, dogs, cats, rabbits, rats, mice and the like. In certain embodiments, the subject is a human.

The adhesive compositions described herein can be used in association with a wide array of medical articles. Non-limiting examples of such articles include wound dressings or coverings, medical dressings, incise films or drapes, surgical dressings or drapes, medical tapes, athletic tapes, surgical tapes, sensors, electrodes, ostomy appliances, or related components such as sealing rings, catheters, connector fittings, catheter hubs, catheter adapters, fluid delivery tubes, electrical wires and cables, negative pressure wound therapy components, surgical drains, wound draining components, IV site dressings such as peripheral IV dressings, prostheses, stoma pouches, buccal patches, transdermal patches, dentures, hairpieces, bandages, diapers, and medical padding such as liposuction padding, hygiene pads, corn and callous pads, toe cushioning pads, and pads for protecting and cushioning tube sites such as tracheotomy tubes. The adhesive product may include one or more faces, regions, and/or surfaces to which the adhesive compositions of the present subject matter are applied. Forming a layer, coating, or other region of adhesive on an article enables the article to be adhered to a wide range of surfaces, including skin. It will be understood that the present subject matter is not limited to any of these articles. Instead, the subject matter includes the use of the adhesive compositions with other articles besides those noted herein.

In certain aspects, the adhesive product is a dressing or drape. Dressings and drapes can include a uniform coating of the adhesive and can be non-patterned in at least one region, along an underside or face of the substrate layer. Dressings and drapes can be cut or otherwise appropriately sized by a medical practitioner prior to application. Dressings and drapes, prior to cutting, can be available in a wide range of sizes such as square shapes of 100 mm by 100 mm, or larger or rectangular shapes of 100 mm by 200 mm or larger. The term "drape" as used herein can refer to even larger articles. In some embodiments, the adhesive product is a surgical tape. In other embodiments, the adhesive product is used for wound care.

Adhesive Layer

The adhesive layer is disposed on at least a portion of the substrate layer, wherein the term "disposed" is not intended to imply that that the adhesive layer and the substrate layer are in direct contact with one another. In certain aspects, one or more intervening layers are located between the adhesive layer and the substrate layer within the adhesive product. In certain aspects, at least a portion of the adhesive layer directly contacts at least a portion of the substrate layer.

In certain versions, the adhesive product includes a continuous adhesive layer, i.e., the adhesive layer covers the entirety of the substrate layer or adhesive product face. In other versions the adhesive product includes a non-continuous adhesive layer, such that at least one region of adhesive is disposed on a face of the substrate layer and at least one adhesive-free region is defined on the face. In certain versions using a non-continuous adhesive layer, an adhesive region in the form of a strip or band is provided that extends around at least a periphery of a face of the substrate layer. One or more adhesive-free regions may be defined on other areas of the substrate layer face such as within a central or interior region of the substrate layer. The adhesive layer can be pattern coated. The adhesive layer can also be melt-blown.

The coat weight of the adhesive layer of the adhesive product can, for example, range from about 15 gram/m$^2$ (gsm) to about 135 gsm, e.g., from about 15 gsm to about 87 gsm, from about 27 gsm to about 99 gsm, from about 39 gsm to about 111 gsm, from about 51 gsm to about 123 gsm, or from about 63 gsm to about 135 gsm. In terms of upper limits, the adhesive layer coat weight can be less than about 135 gsm, e.g., less than about 123 gsm, less than about 111 gsm, less than about 99 gsm, less than about 87 gsm, less than about 75 gsm, less than 63 gsm, less than about 51 gsm, less than about 39 gsm, less than about 27 gsm. In terms of lower limits, the adhesive coat weight is at least about 15 gsm, at least about 27 gsm, at least about 39 gsm, at least about 51 gsm, at least about 63 gsm, at least about 87 gsm, at least about 99 gsm, at least about 111 gsm, or at least about 123 gsm. Higher coat weights, e.g., at least about 135 gsm, and lower coat weights, e.g., less than about 15 gsm, are also contemplated.

In certain aspects, the adhesive composition is formulated as a wet blend prior to coating. The wet blend can include an organic solvent. In some embodiments, the organic solvent is methanol. The concentration of solvent in the wet blend can, for example, range from about 4 wt % to about 16 wt %, e.g., from about 4 wt % to about 11.2 wt %, from about 5.2 wt % to about 12.4 wt %, from about 6.4 wt % to about 13.6 wt %, from about 7.6 wt % to about 14.8 wt %, or from about 8.9 wt % to about 16 wt %. In terms of upper limits, the solvent concentration in the wet blend can be less than about 16 wt %, e.g., less than about 14.8 wt %, less than about 13.6 wt %, less than about 12.4 wt %, less than about 11.2 wt %, less than about 10 wt %, less than about 8.8 wt %, less than about 7.6 wt %, less than about 6.4 wt %, or less than about 5.2 wt %. Higher solvent concentrations, e.g., at least about 16 wt %, and lower solvent concentrations, e.g., less than about 4 wt %, are also contemplated.

The concentrations of solids in the wet blend can, for example, range from about 15 wt % to about 60 wt %, e.g., from about 15 wt % to about 42 wt %, from about 19.5 wt % to about 46.5 wt %, from about 24 wt % to about 51 wt %, from about 28.5 wt % to about 55.5 wt %, or from about 33 wt % to about 60 wt %. In terms of upper limits, the solids concentration in the wet blend can be less than about 60 wt %, e.g., less than about 55.5 wt %, less than about 51 wt %, less than about 46.5 wt %, less than about 42 wt %, less than about 37.5 wt %, less than about 33 wt %, less than about 28.5 wt %, less than about 24 wt %, or less than about 19.5 wt %. In terms of lower limits, the solids concentration in the wet blend can be at least about 15 wt %, e.g., at least about 19.5 wt %, at least about 24 wt %, at least about 28.5 wt %, at least about 33 wt %, at least about 37.5 wt %, at least about 42 wt %, at least about 46.5 wt %, at least about 51 wt %, or at least about 55.5 wt %. Higher solids concentrations, e.g., at least about 60 wt %, and lower solids concentrations, e.g., less than about 15 wt %, are also contemplated.

The adhesive layer of the adhesive product can be applied using standard coating techniques, such as curtain coating, gravure coating, reverse gravure coating, offset gravure coating, roller coating, brushing, knife-over roll coating, air knife coating metering rod coating, reverse roll coating, doctor knife coating, dipping, die coating, spraying, and the like. The application of these coating techniques is well known in the industry and can effectively be implemented by one skilled in the art. Co-extrusion techniques can also be utilized.

In certain aspects, the coating of the adhesive layer involves the use of a coating rod or bar positioned across from the substrate layer at a particular gap distance. The bar gap used during coating of the adhesive layer can, for example, range from about 5 mil to about 15 mil, e.g., from about 5 mil to about 11 mil, from about 6 mil to about 12 mil, from about 7 mil to about 13 mil, from about 8 mil to about 14 mil, or from about 9 mil to about 15 mil. In terms of upper limits, the bar gap can be less than about 15 mil, less than about 14 mil, less than about 13 mil, less than about 12 mil, less than about 11 mil, less than about 10 mil, less than about 9 mil, less than about 8 mil, less than about 7 mil, or less than about 6 mil. In terms of lower limits, the bar gap can be at least about 5 mil, e.g., at least about 6 mil, at least about 7 mil, at least about 8 mil, at least about 9 mil, at least about 10 mil, at least about 11 mil, at least about 12 mil, at least about 13 mil, or at least about 14 mil. Larger bar gaps, e.g., at least about 15 mil, and smaller bar gaps, e.g., less than about 5 mil, are also contemplated.

After coating the wet blend of the adhesive composition, the adhesive layer can be dried by evaporating, for example, the solvent component of the wet blend. In some embodiments, the adhesive layer is dried at room temperature for a first period of time, such as for example approximately 5 minutes, and then dried at an elevated temperature, such as for example 260° F. (127° C.), for a second period of time, such as for example 10 minutes. The temperature for drying for a second period of time may also be 240° F. (116° C.), 210° F. (99° C.), 180° F. (82° C.), or 120° F. (49° C.).

Substrate Layer

The materials and configuration of the substrate layer can be selected to provide a thin and flexible layer that can optionally be permeable to water vapor. In some embodiments, the substrate layer includes a water-proof, flexible, non-adhesive film. In certain aspects the substrate layer includes a polyethylene film, a polyurethane film, a polyvinylchloride film, a polyethylene foam, a polyurethane foam, a polyvinylchloride foam, nonwoven polyurethane, nonwoven elastomeric polyester, knitted fabric, woven fabric, or combinations thereof.

The substrate layer can be sufficiently conformable to conform to the contours of skin to which it will be applied.

The substrate layer can be porous, non-porous, woven or nonwoven or a foam film. The substrate layer can include, for example, non-woven meshes; woven meshes of fiberglass or acetate; gauze; polyurethane foams; polymeric films including polyolefins (linear and branched), halogenated polyolefins, polyamides, polystyrenes, nylon, polyesters, polyester copolymers, polyurethanes, polysulfones, styrene-maleic anhydride copolymers, styrene-acrylonitrile copolymers, ionomers based on sodium or zinc salts of ethylene methacrylic acid, polymethyl methacrylates, cellulosics, acrylic polymers and copolymers, polycarbonates, polyacrylonitriles, and ethylene-vinyl acetate copolymers; composite wound dressings, and adhesive-coated, thin-film dressings.

The substrate layer can include an untreated film that is amenable to adsorption. Alternatively, the substrate layer can be treated by first exposing the layer to an electron discharge treatment, e.g., corona treatment, at a surface. A surface of the substrate layer can be plasma treated, chemically treated or solvent washed. Examples of pretreated films suitable for use in the substrate layer of the disclosed adhesive product include the PET films available from DuPont Teijin Films under the designation ST504 (one side treated) and ST505 (both sides treated).

In some embodiments, a surface of the substrate layer is roughened to improve adhesion and to increase the surface area of the substrate surface. With increased surface area, such as with roughened surfaces and foamed substrates, the adhesion of the adhesive layer or activity of the bioactive compound can be increased.

The substrate layer can be a single-layered film or it can itself be a multi-layered construction. The multi-layered construction can include, for example, coextruded films and laminated films. The multi-layered constructions have two or more layers. In some embodiments, the substrate layer includes from two to seven layers. In some embodiments, the substrate layer includes from three to five layers. The layers of such multi-layered constructions and polymer films can have the same composition and/or size as one another, or they can be different.

The thickness of the substrate layer can, for example, range from about 10 microns to about 80 microns, e.g., from about 10 microns to about 52 microns, from about 17 microns to 59 microns, from about 24 microns to about 66 microns, from about 31 microns to about 73 microns, or from about 38 microns to about 80 microns. In terms of upper limits, the substrate layer thickness can be less than about 80 microns, e.g., less than about 73 microns, less than about 66 microns, less than about 59 microns, less than about 52 microns, less than about 45 microns, less than about 38 microns, less than about 31 microns, less than about 24 microns, or less than about 17 microns. In terms of lower limits, the substrate layer thickness can be at least about 10 microns, e.g., at least about 17 microns, at least about 24 microns, at least about 31 microns, at least about 38 microns, at least about 45 microns, at least about 52 microns, at least about 59 microns, at least about 66 microns, or at least about 73 microns. Larger thicknesses, e.g., at least about 80 microns, and smaller thicknesses, e.g., less than about 10 microns, are also contemplated.

Release Liner

In some embodiments, the adhesive product further comprises a release liner. One face of the release liner can be directly adjacent to the adhesive layer, or there can be one or more intervening layers between the adhesive layer and the release liner. In some cases, one face of the adhesive layer is directly adjacent to the release liner, and an opposite face of the adhesive layer is directly adjacent to the substrate layer.

The releasable liner can function as a protective cover such that the release liner remains in place until the adhesive is ready for attachment to a subject. If a liner or release liner is included in the adhesive product, a wide array of materials and configurations can be used for the liner. In many embodiments, the liner is a paper or paper-based material. In many other embodiments, the liner is a polymeric film of one or more polymeric materials. Typically, at least one face of the liner is coated with a release material such as a silicone or silicone-based material. As will be appreciated, the release coated face of the liner is placed in contact with the otherwise exposed face of the outer adhesive layer. Prior to application of the label to a surface of interest, the liner is removed to thereby expose the adhesive layer of the adhesive product. The liner can be in the form of a single sheet. Alternatively, the liner can be in the form of multiple sections or panels.

The thickness of the release liner can, for example, range from about 0.5 mil to about 8 mil, e.g., from about 0.5 mil to about 5 mil, from about 1.25 mil to about 5.75 mil, from about 2 mil to about 6.5 mil, from about 2.75 mil to about 7.25 mil, or from about 3.5 mil to about 8 mil. In terms of upper limits, the release liner thickness can be less than about 8 mil, e.g., less than about 7.25 mil, less than about 6.5 mil, less than about 5.75 mil, less than about 5 mil, less than about 4.25 mil, less than about 3.5 mil, less than about 2.75 mil, less than about 2 mil, or less than about 1.25 mil. In terms of lower limits, the release liner thickness can be at least about 0.5 mil, e.g., at least about 1.25 mil, at least about 2 mil, at least about 2.75 mil, at least about 3.5 mil, at least about 4.25 mil, at least about 5 mil, at least about 5.75 mil, at least about 6.5 mil, or at least about 7.25 mil. Larger thicknesses, e.g., at least about 8 mil, and smaller thicknesses, e.g., less than about 0.5 mil, are also contemplated.

Methods of Bioactive Compound Release

Also provided are methods for the release of a bioactive compound to a subject using the disclosed adhesive composition. The methods include providing a disclosed adhesive product and contacting the adhesive layer of the adhesive product to the subject. In certain aspects, the adhesive layer is contacted with a biological skin surface of the subject, thereby delivering the bioactive compound of the adhesive product to the subject. In some embodiments, the biological skin surface is at or proximate to a wound or surgical site of the subject.

Methods for Producing an Adhesive Composition

Also provided are methods for producing the disclosed adhesive compositions. The methods include providing: 1) at least one adhesive of any of the types and amounts described herein, 2) a phase-separated hydrophilic material, and 3) a bioactive compound. At least one adhesive may comprise at least one adhesive of an alcohol-functionalized acrylic adhesive, an alcohol-functionalized silicone adhesive, a carboxyl-functionalized acrylic adhesive, and a carboxyl-functionalized silicone adhesive. The phase-separated hydrophilic material may be of any of the types and amounts described above. At least one bioactive compound may be of any of the types and amounts described above. The methods also include: 1) providing the adhesive, the phase-separated hydrophilic material, and the bioactive compound; and 2) combining at least one adhesive, the phase-separated hydrophilic material, and the bioactive compound to produce the adhesive composition. In many embodiments, at least one adhesive may comprise an acrylic adhesive, an alcohol-functionalized acrylic adhesive, a carboxyl-functionalized acrylic adhesive, a silicone adhesive, an alcohol-functionalized silicone adhesive, and a carboxyl-functionalized silicone adhesive. In some embodiments, the combining comprises blending the components in solvents, such as alcohols, toluene, heptanes, and the like, until a homogeneous blend is obtained. The blending time can be, for example, approximately 2 hours. Various methods of blending are known in the art, and any method that produces a homogeneous blend can be suitable for use in producing the adhesive composition.

Embodiments

The following embodiments are contemplated. All combinations of features and embodiments are contemplated.

Embodiment 1: An adhesive composition comprising: an adhesive, wherein the adhesive comprises at least one adhesive of an alcohol-functionalized acrylic adhesive, a carboxyl-functionalized acrylic adhesive, an alcohol-functionalized silicone adhesive, and a carboxyl-functionalized silicone adhesive; at least one phase-separated hydrophilic material; and at least one bioactive compound.

Embodiment 2: An adhesive composition comprising: at least one adhesive of an acrylic adhesive and a silicone adhesive; a phase-separated hydrophilic material; and at least one bioactive compound.

Embodiment 3: An embodiment of embodiment 2, wherein the acrylic adhesive is an alcohol-functionalized acrylic adhesive.

Embodiment 4: An embodiment of embodiment 2, wherein the acrylic adhesive is a carboxyl-functionalized acrylic adhesive.

Embodiment 5: An embodiment of embodiment 2, wherein the silicone adhesive is an alcohol-functionalized silicone adhesive.

Embodiment 6: An embodiment of embodiment 2, wherein the silicone adhesive is a carboxyl-functionalized silicone adhesive.

Embodiment 7: An adhesive composition comprising: at least one adhesive of an alcohol-functionalized acrylic adhesive, an alcohol-functionalized silicone adhesive, a carboxyl-functionalized acrylic adhesive, and a carboxyl-functionalized silicone adhesive; at least one phase-separated hydrophilic material; and at least one bioactive compound.

Embodiment 8: An embodiment of embodiment 7, wherein at least one of the silicone adhesive and the acrylic adhesive is an alcohol-functionalized adhesive.

Embodiment 9: An embodiment of embodiment 7, wherein at least one of the silicone adhesive and the acrylic adhesive is a carboxyl-functionalized adhesive.

Embodiment 10: An embodiment of any of the embodiments of embodiment 1-9, wherein the concentration of the phase-separated hydrophilic material in the adhesive composition ranges from about 2 wt % to about 40 wt %.

Embodiment 11: An embodiment of any of the embodiments of embodiment 1-10, wherein the concentration of the bioactive compound in the adhesive composition ranges from about 1 wt % to about 10 wt %.

Embodiment 12: An embodiment of any of the embodiments of embodiment 1-11, wherein the concentration of at least one adhesive of an alcohol-functionalized acrylic adhesive, an alcohol-functionalized silicone adhesive, a carboxyl-functionalized acrylic adhesive, and a carboxyl-functionalized silicone adhesive in the adhesive composition ranges from about 60 wt % to about 95 wt %.

Embodiment 13: An embodiment of any of the embodiments of embodiment 1-12, wherein the bioactive compound comprises an antimicrobial agent.

Embodiment 14: An embodiment of embodiment 13, wherein the antimicrobial agent comprises a bis-biguanide salt.

Embodiment 15: An embodiment of embodiment 14, wherein the bis-biguanide salt comprises a chlorhexidine salt.

Embodiment 16: An embodiment of embodiment 15, wherein the chlorhexidine salt comprises chlorhexidine digluconate.

Embodiment 17: An embodiment of any of the embodiments of embodiment 1-16, wherein the phase-separated hydrophilic material comprises at least one of silicon dioxide, zinc oxide, titanium dioxide, calcium carbonate, starches, crystalline cellulose, microcrystalline cellulose, carboxylmethyl cellulose, crospovidone, or clay.

Embodiment 18: An embodiment of any embodiment of embodiments 1-17, the adhesive composition comprising less than about 1 wt % microcrystalline cellulose.

Embodiment 19: An embodiment of any of the embodiments of embodiment 1-17, having a release rate of the bioactive compound into water, wherein the release rate is at least about 50 μg/cm2 within 90 minutes of contact of the adhesive composition with water.

Embodiment 20: An embodiment of embodiment 19, wherein the concentration of the phase-separated hydrophilic material in the adhesive composition ranges from 2 wt % to 40 wt %, wherein the concentration the bioactive compound in the adhesive composition ranges from 1 wt % to 10 wt %, and wherein the release rate is at least about 120 μg/cm2 within 90 minutes of contact of the adhesive composition with water.

Embodiment 21: An embodiment of embodiment 19, wherein the concentration of the phase-separated hydrophilic material in the adhesive composition ranges from 7 wt % to 15 wt %, wherein the concentration the acrylic adhesive in the adhesive composition ranges from 80 wt % to 90 wt %, and wherein the release rate is at least about 120 μg/cm2 within 90 minutes of contact of the adhesive composition with water.

Embodiment 22: An embodiment of embodiment 19, wherein the concentration the bioactive compound in the adhesive composition ranges from 4 wt % to 8 wt %, wherein the concentration of the acrylic adhesive ranges from 80 wt % to 90 wt %, and wherein the release rate is at least about 120 μg/cm2 within 90 minutes of contact of the adhesive composition with water.

Embodiment 23: An embodiment of embodiment 19, wherein the phase-separated hydrophilic material comprises microcrystalline cellulose, wherein the bioactive compound comprises chlorhexidine digluconate, and wherein the release rate is at least about 120 μg/cm2 within 90 minutes of contact of the adhesive composition with water.

Embodiment 24: An embodiment of any of the embodiments of embodiment 1-23, having antimicrobial activity resulting in at least about 4 log reduction in a *Pseudomonas aeruginosa* population within 90 minutes of contact of the adhesive composition with the population.

Embodiment 25: An embodiment of any of the embodiments of embodiment 1-24, having antimicrobial activity resulting in at least about 4 log reduction in an *Escherichia* coli population within 90 minutes of contact of the adhesive composition with the population.

Embodiment 26: An embodiment of any of the embodiments of embodiment 1-25, having antimicrobial activity resulting in at least about 4 log reduction in a *Staphylococcus aureus* population within 90 minutes of contact of the adhesive composition with the population.

Embodiment 27: An embodiment of any of the embodiments of embodiment 1-26, having antimicrobial activity resulting in at least about 4 log reduction in a *Candida albicans* population within 90 minutes of contact of the adhesive composition with the population.

Embodiment 28: An embodiment of any of the embodiments of embodiment 1-27, having antimicrobial activity resulting in at least about 0.1 log reduction in an *Aspergillus brasiliensis* population within 90 minutes of contact of the adhesive composition with the population.

Embodiment 29: An embodiment of any of the embodiments of embodiment 1-28, having a grade 2 cytotoxicity.

Embodiment 30: An embodiment of any of the embodiments of embodiment 1-29, having a Primary Irritation Index value of less than or equal to 2.

Embodiment 31: An adhesive product comprising: a substrate layer; and an adhesive layer disposed on at least a portion of the substrate layer, wherein the adhesive layer comprises the adhesive composition of any of the embodiments of embodiment 1-30.

Embodiment 32: An embodiment of embodiment 31, wherein the substrate layer comprises a polyethylene film, a polyurethane film, a polyvinylchloride film, a polyethylene foam, a polyurethane foam, a polyvinylchloride foam, nonwoven polyurethane, nonwoven elastomeric polyester, knitted fabric, woven fabric, or combinations thereof.

Embodiment 33: An embodiment of embodiment 31 or 32, wherein the substrate layer comprises a waterproof, flexible, non-adhesive film.

Embodiment 34: An embodiment of any of the embodiments of embodiment 31-33, wherein the adhesive product is configured for conformable topical application to biological skin.

Embodiment 35: An embodiment of any of the embodiments of embodiment 31-34, wherein the adhesive product is a pressure sensitive adhesive bandage, a wound covering, a medical dressing, a surgical dressing, a surgical drape, a surgical tape, or a medical tape.

Embodiment 36: An embodiment of any of the embodiments of embodiment 31-35, wherein at least a portion of the adhesive layer directly contacts at least a portion of the substrate layer.

Embodiment 37: An embodiment of any of the embodiments of embodiment 31-36, further comprising: a release liner.

Embodiment 38: A method for the release of a bioactive compound to a subject, the method comprising: providing the adhesive product of any of the embodiments of embodiment 31-37; and contacting the adhesive layer of the adhesive product to a biological skin surface of the subject, thereby delivering the bioactive compound of the adhesive product to the subject.

Embodiment 39: An embodiment of embodiment 38, wherein the biological skin surface is proximate to a wound or surgical site of the subject.

Embodiment 40: An embodiment of embodiment 38 or 39, wherein the subject is human.

Embodiment 41: A method for producing an adhesive composition, the method comprising: 1) providing at least one adhesive of an alcohol-functionalized acrylic adhesive, an alcohol-functionalized silicone adhesive, a carboxyl-functionalized acrylic adhesive, and a carboxyl-functionalized silicone adhesive, at least one phase-separated hydrophilic material, and at least one bioactive compound; and combining the alcohol-functionalized acrylic adhesive, the phase-separated hydrophilic, and the bioactive compound to produce the adhesive composition; and 2) combining the adhesive, the phase-separated hydrophilic material, and the bioactive compound to produce the adhesive composition.

Embodiment 42: An embodiment of embodiment 41, wherein the adhesive composition comprises: 60 wt % to 95 wt % of at least one adhesive of an alcohol-functionalized acrylic adhesive, an alcohol-functionalized silicone adhesive, a carboxyl-functionalized acrylic adhesive, and a carboxyl-functionalized silicone adhesive; 2 wt % to 40 wt % of the phase-separated hydrophilic material; and 1 wt % to 10 wt % of the bioactive compound.

Embodiment 43: An embodiment of embodiment 41 or 42, wherein the bioactive compound comprises chlorhexidine digluconate.

Embodiment 44: An embodiment of any of the embodiments of embodiment 41-43, wherein the phase-separated hydrophilic material comprises at least one of silicon dioxide, zinc oxide, titanium dioxide, calcium carbonate, starches, crystalline cellulose, microcrystalline cellulose, carboxylmethyl cellulose, crospovidone, or clay.

Embodiment 45: An embodiment of any of the embodiments of embodiment 41-44, wherein the adhesive composition has a release rate of the bioactive compound into water, and wherein the release rate is at least about 50 μg/cm2 within 90 minutes of contact of the adhesive composition with water.

The present disclosure will be better understood in view of the following non-limiting examples.

Examples

The following examples are added to illustrate the benefits of disclosed adhesive compositions and are non-limiting.

TABLE 1A

| | OH—functionalized acrylic adhesive (%) | COOH—functionalized acrylic adhesive (%) | Phase separated hydrophilic material | Bioactive (%) | Other (%) |
|---|---|---|---|---|---|
| Example 1 | 90 | 0 | 5 | 5 | 0 |
| Example 2 | 85 | 0 | 10 | 5 | 0 |
| Example 3 | 86.5 | 0 | 8.5 | 5 | 0 |
| Example 4 | 87.5 | 0 | 7.5 | 5 | 0 |
| Comp. A | 0 | 66 | 30 | 4 | 0 |
| Comp. B | 0 | 83.5 | 10 | 4 | 2.5 |
| Comp. C | 0 | 70 | 22.5 | 5 | 2.5 |

The adhesives of Examples 1-4 and Comparative Examples A-C were laminated between a stiff polyester layer and a 5-gsm polyurethane layer. This configuration allowed the adhesive composition to remain unfolded and un-sticky during testing with a rigid acrylic adhesive tape attached to the polyurethane film for the reinforcement. Samples measuring 2 inches (5.08 cm) by 1 inch (2.54 cm) were place in 25 ml demineralized water on a shaker. At regular time points, 500 μl of solution was removed and analyzed by UV-spectrophotometry. Spectrophotometric readings at a wavelength of 239 nm were used to measure the CHG concentration.

The antimicrobial agent release results shown in Table 1A below demonstrate that the disclosed adhesive compositions demonstrated significantly higher release rates and release percentages of the antimicrobial agent as compared to those of the comparative examples.

TABLE 1B

| CHG release results | | | | | | | |
|---|---|---|---|---|---|---|---|
| | Phase-separated hydrophilic material type | Phase-separated hydrophilic material conc. (wt %) | CHG conc. (wt %) | CHG release rate (μg/cm²) 60 min | CHG release rate (μg/cm²) 90 min | CHG release amount (%) 60 min | CHG release amount (%) 90 min |
| Example 1 | $SiO_2$ | 5 | 5 | 66.1 | 119.4 | 29 | 53 |
| Example 2 | $SiO_2$ | 10 | 5 | 91.3 | 157.3 | 41 | 70 |
| Example 3 | $SiO_2$ | 8.5 | 5 | NA | NA | NA | NA |
| Example 4 | $SiO_2$ | 7.5 | 5 | 87.0 | 132.5 | 39 | 59 |
| Comp. A | Microcrystalline Cellulose A | 30 | 4 | — | 35.4-47.8* | — | 10-13* |
| Comp. B | Microcrystalline Cellulose B | 10 | 4 | 22.4 | 27.1 | 12 | 15 |
| Comp. C | Microcrystalline Cellulose B | 22.5 | 5 | 54.1-57.1 | 95.4-105.2 | 24-25 | 42-47 |

*CHG release rate at 2 hours.

Additional adhesive compositions described in Table 1C were prepared in accordance with Table 1B.

TABLE 1C

| Bioactive Other | | | | | | | |
|---|---|---|---|---|---|---|---|
| | OH—functionalized acrylic adhesive (%) | COOH—functionalized acrylic adhesive (%) | Phase separated hydrophilic material (SiO2, %) | Phase separated hydrophilic material (Microcrystalline Cellulose, %) | Phase separated hydrophilic material (Crospovidone, %) | Bioactive (%) | Other (%) |
| Example 5 | 88.5 | 0 | 6.5 | 0 | 0 | 5 | 0 |
| Comp. D | 0 | 78.5 | 0 | 15 | 0 | 4 | 2.5 |
| Comp. E | 0 | 77.5 | 0 | 15 | 0 | 5 | 2.5 |
| Comp. F | 0 | 71 | 0 | 22.5 | 0 | 4 | 2.5 |
| Comp. G | 0 | 77.5 | 0 | 0 | 15 | 5 | 2.5 |
| Comp. H | NA | NA | NA | NA | NA | NA | NA |

The antimicrobial efficacies of these adhesive compositions were measured according to the standard protocol ASTM E2315-16. Square pieces of adhesive 5 cm×5 cm were aseptically cut. Microorganisms were grown with tryptic soy agar (TSA) at 32.5° C. for 18 to 24 hours, and then harvested with sterile water to achieve a final concentration between $1.0\times10^7$ cfu/ml to $5.0\times10^7$ cfu/ml, wherein "cfu" refers to colony forming units. Under a class-100 biological cabinet, the 5 cm×5 cm adhesive films were inoculated with 50 μl of the prepared challenge organism to achieve an inoculum of $1.0\times10^6$ to $5.0\times10^6$ cfu of the samples. The inoculated samples were covered with a 35 mm diameter sterile glass to assure that the inoculum was in intimate contact with the adhesive and that the inoculum did not spread beyond the edge of the test sample. The inoculated test sample was held at 31-32° C. and 75% relative humidity. The identical procedure is performed on a placebo (identical adhesive not containing the CHG).

After a 90-minute contact time, the glass covers were carefully separated from both the placebo and inoculated samples, and were placed into 100 ml of Dey-Engley Neutralizing Broth and sonicated for 10 minutes. Enumeration of the recovered microorganisms was performed by pour plating onto TSA (bacterial) or SDA (yeast and mold) 2×10-ml aliquots ($10^{-1}$ dilution), 2× 1-ml aliquots ($10^{-2}$ dilution), 2× 0.1-ml aliquots ($10^{-3}$ dilution), 10-μl aliquots ($10^{-4}$ dilution), and 1 ml into 9.9 ml D/E broth aliquots ($10^{-5}$ dilution). The log reduction was then calculated by subtracting the $\log_{10}$ cfu from the test sample to contact and the $\log_{10}$ cfu from the test sample after 90 minutes of contact.

The antimicrobial efficacy results shown in Table 2A below demonstrate that of the materials tested, only the exemplary adhesive composition was surprisingly effective in reducing both the populations of the tested bacterial and yeast cultures by a factor at least about log 4, and the population of the tested fungal mold by a factor at least about log 0.1. The comparative examples were unable to reduce both the populations of the tested bacterial and yeast cultures and the population of the tested fungal mold in the same manner.

TABLE 2A

| Antimicrobial efficacy results | | | | | | | | |
|---|---|---|---|---|---|---|---|---|
| | Ex. 3 | Ex. 5 | Comp. C | Comp. D | Comp. E | Comp. F | Comp. G | Comp. H |
| 90-Minute log reduction | | | | | | | | |
| *P. aeruginosa* | ≥5.59 | ≥5.11 | ≥5.52 | ≥5.56 | ≥5.53 | ≥5.60 | ≥5.53 | ≥5.11 |
| *E. coli* | ≥5.36 | ≥5.11 | ≥5.54 | 2.51 | 2.98 | 4.41 | ≥5.58 | ≥5.57 |
| *S. aureus* | ≥5.11 | ≥5.18 | ≥5.58 | 2.30 | 2.60 | 3.54 | 3.82 | ≥5.52 |
| *C. albicans* | ≥5.11 | ≥5.48 | 4.00 | 3.42 | 4.07 | 3.89 | ≥5.26 | ≥5.20 |
| *A. brasiliensis* | 2.34 | 3.16 | 1.93 | 3.62 | 3.19 | 3.73 | 3.49 | 2.44 |
| *S. epidermidis* | ≥5.60 | NA | ≥5.51 | NA | NA | NA | NA | NA |
| *E. faecalis* [VRE] | ≥5.63 | NA | ≥5.58 | NA | NA | NA | NA | NA |
| *E. aerogenes* | ≥5.59 | NA | ≥5.56 | NA | NA | NA | NA | NA |

Additional adhesive compositions were prepared in accordance with Table 2B.

TABLE 2B

| Compositions | OH—functionalized adhesive (%) | COOH—functionalized acrylic adhesive (%) | Phase separated hydrophilic material | Bio-active | Other |
|---|---|---|---|---|---|
| Example 3 | 86.5 | 0 | 8.5 | 5 | 0 |
| Example 5 | 88.5 | 0 | 6.5 | 5 | 0 |
| Comp. C | 0 | 70 | 22.5 | 5 | 2.5 |
| Neg. Cont | High density polyethylene (HDPE) | | | | |
| Pos. Cont. | Latex/Composition: natural rubber latex, zinc carbamate accelerators, zinc oxide, and titanium dioxide | | | | |

The cytotoxicities of these adhesive compositions were measured according to standard protocol ISO10993-5:2009 using mouse fibroblast cell line L-929. The cells were incubated in 10-$cm^2$ wells to obtain sub-confluent monolayers of cells. The growth medium was then replaced in each well by 2 ml of agarose. Test articles prepared in a square were placed on the solidified agarose surface. The wells were incubated for a period of 24 hours and then observed under a microscope.

The cytotoxicity results shown in Table 3 below demonstrate that the disclosed adhesive composition showed no evidence of causing cell lysis or other cytotoxicity effects to the tested cells, indicating that the adhesive composition meets requirements associated with medical products.

TABLE 3

| Cytotoxicity results | | | |
|---|---|---|---|
| | Zone of lysis (mm) | Cytotoxicity grade | Reactivity |
| Example 3 | | | |
| Test 1 | 0 | 0 | None |
| Test 2 | 0 | 0 | None |
| Test 3 | 0 | 0 | None |
| Example 5 | | | |
| Test 1 | 0 | 0 | None |
| Test 2 | 0 | 0 | None |
| Test 3 | 0 | 0 | None |
| Negative control | | | |
| Test 1 | 0 | 0 | None |
| Test 2 | 0 | 0 | None |
| Test 3 | 0 | 0 | None |

TABLE 3-continued

| Cytotoxicity results | | | |
|---|---|---|---|
| | Zone of lysis (mm) | Cytotoxicity grade | Reactivity |
| Positive control | | | |
| Test 1 | 10, 11 | 3, 4 | Moderate to Severe |
| Test 2 | 7, 11 | 3, 4 | Moderate to Severe |
| Test 3 | 9, 11 | 3, 4 | Moderate to Severe |

Cytotoxicity Test method:

For the cytotoxicity test, the release liner was removed and excluded from the preparation. Based on the USP ratio of 120 cm":20 mL, a 60 cm portion of the test article was covered with 10 mL of single strength Minimum Essential Medium supplemented with 5% serum and 2% antibiotics (IX MEM). A single preparation was extracted with agitation at 37° C. for 24 hours. The IX MEM extraction method was conducted in the presence of serum to optimize extraction of both polar and non-polar components. For the testing extract after 24 hours, Comp. C had a 0% lysis and a rating for cytotoxic effect (CTE) score of non-toxic (N).

The likelihood of skin irritation caused by the adhesive composition was measured according to standard protocol ISO10993-10:2010, with results shown in Table 4 below. The results demonstrate that application of the adhesive composition to each of the test animals resulted in no to very slight erythema, and no edema, indicating only a slight irritation response.

TABLE 4

Skin irritation performance results

| | Test score average | Control score average | Individual primary irritation score | Combined primary irritation score | Primary irritation index | Response category |
|---|---|---|---|---|---|---|
| Example 5 | | | | | | |
| Animal 1 | 1 | 0 | 1 | 2 | 0.7 | Slight |
| Animal 2 | 1 | 0 | 1 | | | |
| Animal 3 | 0 | 0 | 0 | | | |
| Example 3 | | | | | | |
| Animal 1 | 0 | 0 | 0 | 0 | 0 | Negligible |
| Animal 2 | 0 | 0 | 0 | | | |
| Animal 3 | 0 | 0 | 0 | | | |
| Comp C | | | | | | |
| Animal 1 | 1.7 | 0 | 1.7 | 5.4 | 1.8 | Slight |
| Animal 2 | 2.0 | 0 | 2.0 | | | |
| Animal 3 | 1.7 | 0 | 1.7 | | | |

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. An adhesive composition comprising:

at least one adhesive, wherein the at least one adhesive is an alcohol-functionalized acrylic adhesive;

at least one phase-separated hydrophilic material selected from the group consisting of silicon dioxide, titanium dioxide, and combinations thereof; and at least one bioactive compound comprising an antimicrobial agent, wherein a concentration of the at least one bioactive compound in the adhesive composition ranges from about 1 wt % to about 10 wt %;

wherein a concentration of the at least one phase-separated hydrophilic material in the adhesive composition ranges from about 7 wt % to about 15 wt %;

wherein a concentration of the at least one adhesive in the at least one adhesive composition ranges from about 80 wt % to about 90 wt %, and wherein the adhesive composition has a release rate of the at least one bioactive compound into water, and wherein the release rate is at least about 50 μg/cm$^2$ within 90 minutes of contact of the adhesive composition with water.

2. The adhesive composition of claim 1, wherein the at least one adhesive is a pressure sensitive adhesive.

3. The adhesive composition of claim 1, wherein the at least one adhesive is a hybrid adhesive.

4. The adhesive composition of claim 1, wherein the antimicrobial agent comprises a bis-biguanide salt.

5. The adhesive composition of claim 4, wherein the bis-biguanide salt comprises a chlorhexidine salt.

6. The adhesive composition of claim 5, wherein the chlorhexidine salt comprises chlorhexidine digluconate.

7. The adhesive composition of claim 1, having a release rate of the at least one bioactive compound into water, and wherein the release rate is at least about 75 μg/cm$^2$ within 90 minutes of contact of the adhesive composition with water.

8. The adhesive composition of claim 1, having a release rate of the at least one bioactive compound into water, and wherein the release rate is at least about 100 μg/cm$^2$ within 90 minutes of contact of the adhesive composition with water.

9. The adhesive composition of claim 1, wherein a release rate of the at least one bioactive compound into water is at least about 120 μg/cm$^2$ within 90 minutes of contact of the adhesive composition with water.

10. The adhesive composition of claim 1, wherein the at least one bioactive compound comprises chlorhexidine digluconate, and wherein the release rate is at least about 120 μg/cm$^2$ within 90 minutes of contact of the adhesive composition with water.

11. The adhesive composition of claim 1, wherein the concentration the at least one bioactive compound in the at least one adhesive composition ranges from about 4 wt % to about 8 wt %, wherein the concentration of the at least one adhesive ranges from about 80 wt % to about 90 wt %, and wherein the release rate is at least about 120 μg/cm$^2$ within 90 minutes of contact of the adhesive composition with water.

12. The adhesive composition of claim 1, having antimicrobial activity resulting in at least a 4 log reduction in a *Pseudomonas aeruginosa* population within 90 minutes of contact of the adhesive composition with the population.

13. The adhesive composition of claim 1, having antimicrobial activity resulting in at least a 4 log reduction in an *Escherichia coli* population within 90 minutes of contact of the adhesive composition with the population.

14. The adhesive composition of claim 1, having antimicrobial activity resulting in at least a 4 log reduction in a

*Staphylococcus aureus* population within 90 minutes of contact of the adhesive composition with the population.

15. The adhesive composition of claim 1, having antimicrobial activity resulting in at least a 4 log reduction in a *Candida albicans* population within 90 minutes of contact of the adhesive composition with the population.

16. The adhesive composition of claim 1, having antimicrobial activity resulting in at least a 0.1 log reduction in an *Aspergillus brasiliensis* population within 90 minutes of contact of the adhesive composition with the population.

17. The adhesive composition of claim 1, having a cytotoxicity grade of less than or equal to 2.

18. The adhesive composition of claim 1, having a Primary Irritation Index value of less than or equal to 2.

19. An adhesive product comprising:

a substrate layer; and an adhesive layer disposed on at least a portion of a surface of the substrate layer, wherein the adhesive layer comprises the adhesive composition of claim 1.

20. The adhesive product of claim 19, wherein the substrate layer comprises a polyethylene film, a polyurethane film, a polyvinylchloride film, a polyethylene foam, a polyurethane foam, a polyvinylchloride foam, nonwoven polyurethane, nonwoven elastomeric polyester, knitted fabric, woven fabric, or combinations thereof.

21. The adhesive product of claim 19, wherein the substrate layer comprises a waterproof, flexible, non-adhesive film.

22. The adhesive product of claim 19, wherein the adhesive product is configured for conformable topical application to biological skin.

23. The adhesive product of claim 19, wherein the adhesive product is a pressure sensitive adhesive bandage, a wound covering, a medical dressing, a surgical dressing, a surgical drape, a surgical tape, an incise drape, or a medical tape.

24. The adhesive product of claim 19, wherein at least a portion of the adhesive layer directly contacts the at least a portion of the substrate layer.

25. The adhesive product of claim 19, further comprising: a release liner.

26. A method for the release of a bioactive compound to a subject in need thereof, the method comprising:

providing the adhesive product of claim 19; and contacting the adhesive layer of the adhesive product to a biological skin surface of the subject, thereby delivering the bioactive compound of the adhesive product to the subject.

27. The method of claim 26, wherein the biological skin surface is proximate to a wound or surgical site of the subject.

28. The method of claim 26, wherein the subject is human.

29. A method for producing an adhesive composition, the method comprising:

providing: 1) at least one adhesive wherein the at least one adhesive is an alcohol-functionalized acrylic adhesive, 2) at least one phase-separated hydrophilic material selected from the group consisting of silicon dioxide, titanium dioxide, and combinations thereof, and 3) at least one bioactive compound comprising an antimicrobial agent; and combining the at least one adhesive, the at least one phase-separated hydrophilic material, and the at least one bioactive compound to produce the adhesive composition, wherein a concentration of the at least one bioactive compound in the adhesive composition ranges from about 1 wt % to about 10 wt %;

wherein a concentration of the at least one phase-separated hydrophilic material in the adhesive composition ranges from about 7 wt % to about 15 wt %;

wherein a concentration of the adhesive in the adhesive composition ranges from about 80 wt % to about 90 wt %, and wherein the adhesive composition has a release rate of the at least one bioactive compound into water, and wherein the release rate is at least about 50 μg/cm$^2$ within 90 minutes of contact of the adhesive composition with water.

30. The method of claim 29, wherein the at least one bioactive compound comprises chlorhexidine digluconate.

* * * * *